US011524931B2

(12) United States Patent
Dumoleijn et al.

(10) Patent No.: US 11,524,931 B2
(45) Date of Patent: Dec. 13, 2022

(54) PROCESS FOR DRYING N,N-DIMETHYL GLYCINATE SALTE

(71) Applicant: Taminco BVBA, Ghent (BE)

(72) Inventors: Kim Dumoleijn, Eede (NL); Kristof Moonen, Hamme (BE); Daan Ruben Scheldeman, Waregem (BE); Angelo Lauwaerts, Ghent (BE); Dieter Ulrichts, Sint-Adries (BE)

(73) Assignee: Taminco BV, Ghent (BE)

( * ) Notice: Subject to any disclaimer, the term of this patent is extended or adjusted under 35 U.S.C. 154(b) by 0 days.

(21) Appl. No.: 16/979,764

(22) PCT Filed: Mar. 12, 2019

(86) PCT No.: PCT/EP2019/056158
§ 371 (c)(1),
(2) Date: Sep. 10, 2020

(87) PCT Pub. No.: WO2019/175169
PCT Pub. Date: Sep. 19, 2019

(65) Prior Publication Data
US 2021/0017121 A1    Jan. 21, 2021

(30) Foreign Application Priority Data

Mar. 13, 2018 (EP) .................................. 18161606
Oct. 22, 2018 (EP) .................................. 18201837

(51) Int. Cl.
| | |
|---|---|
| *C07C 227/40* | (2006.01) |
| *C07C 229/12* | (2006.01) |
| *F26B 3/08* | (2006.01) |
| *F26B 25/00* | (2006.01) |

(52) U.S. Cl.
CPC .......... *C07C 227/40* (2013.01); *C07C 229/12* (2013.01); *F26B 3/082* (2013.01); *F26B 25/001* (2013.01)

(58) Field of Classification Search
CPC ..... C07C 227/40; C07C 229/12; F26B 3/082; F26B 25/001
See application file for complete search history.

(56) References Cited

U.S. PATENT DOCUMENTS

| | | | | |
|---|---|---|---|---|
| 4,968,839 A * | 11/1990 | Noell | .................... | C07C 227/26 562/575 |
| 5,049,250 A | 9/1991 | Chlanda | | |
| 5,268,079 A | 12/1993 | Ochoa Gomez et al. | | |
| 2010/0056817 A1* | 3/2010 | Meunier | ................ | C07C 227/42 556/112 |
| 2012/0202731 A1* | 8/2012 | Mrzena | .............. | C11D 11/0088 510/224 |

FOREIGN PATENT DOCUMENTS

| | | | | |
|---|---|---|---|---|
| DE | 292239 A5 * | 7/1991 | .......... | C07C 227/07 |
| EP | 0201925 A1 | 5/1986 | | |
| JP | 62210007 A | 9/1987 | | |
| WO | WO 2007/107184 A1 | 9/2007 | | |
| WO | WO 2009/016025 A1 | 2/2009 | | |
| WO | WO 2013/174764 A1 | 11/2013 | | |

OTHER PUBLICATIONS

Jones, D., Fluidized bed processing and drying, Pharmaceutical Engineering, 8 pages (Year: 1991).*
DD 292239 (A5), Wagner, A., et al., Process for the preparation of alkali metal salts of n-alkyl-substituted aminoalkanoic acids, English translation abstract, 2 pages (Year: 1991).*
Praia, L., et al., Effects of N,N-dimethylglycine sodium salt on apparent digestibility, vitamin E absorption, and serum proteins in broiler chickens fed a high- or low-fat diet., Poultry Science Ass. Inc,. pp. 1221-1226 (Year: 2013).*
Rychen, G. et al. Safety and efficacy of Taminizer D (dimethylglycine sodium salt) as a feed additive for chickens for fattening, EJ EFSA Journal, Scientific Opinion, pp. 1-12 (Year: 2018).*
Kalmar, D., et al., "Dietary N,N-dimethylglycine supplementation improves nutrient digestibility and attenuates pulmonary hypertension syndrome in broilers"; Journal of Animal Physiology and Animal Nutrition 94, (2010), pp. 339-347.
Notification of Transmittal of the International Search Report and the Written Opinion of the International Searching Authority dated Apr. 9, 2019 for International Application No. PCT/EP2019/056158.
Notification of Transmittal of the International Search Report and the Written Opinion of the International Searching Authority dated Jun. 14, 2019 for International Application No. PCT/EP2019/056165.
Co-pending U.S. Appl. No. 16/979,745, filed Sep. 10, 2020.
USPTO Office Action dated Feb. 1, 2022 received in co-pending U.S. Appl. No. 16/979,745.

* cited by examiner

*Primary Examiner* — Yate' K Cutliff
(74) *Attorney, Agent, or Firm* — Kenrick L. Vidale

(57) ABSTRACT

The application relates to a process for drying a composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, and the use thereof. In the process, the composition, in particular the N,N-di methyl glycinate salt, is dried by feeding the composition into a fluidized bed dryer and subjecting the composition to a heat treatment by contacting the composition in the fluidized bed dryer with a drying gas stream, and during the heat treatment a solution or dispersion of the composition is sprayed onto at least a portion of the composition present in the fluidized bed dryer, or alternatively or in addition the composition, in particular N,N-dimethyl glycinate salt, is fed into a fluidized bed dryer and subjected to heat treatment in the fluidized bed dryer by contacting the composition with a drying gas stream, and the temperature of the composition in the fluidized bed during the heat treatment does not exceed 50° C.

18 Claims, No Drawings

PROCESS FOR DRYING N,N-DIMETHYL GLYCINATE SALTE

CROSS-REFERENCE TO RELATED APPLICATION(S)

This application is a national stage filing under 35 USC § 371 of International Application Number PCT/EP2019/056158, filed on, Mar. 12, 2019 which claims priority to European Application EP 18161606.1 filed on Mar. 13, 2018 and EP 18201837.4 filed on Oct. 22, 2018, the entire disclosures of which are incorporated by reference herein.

FIELD OF THE INVENTION

The application relates to a method for drying a composition comprising an alkali metal salt of a compound of general formula (I) $R^1R^2N$—$CHR^3$—COOM or formula (II) $R^1R^2N$—$CHR^3CHR^3$—COOM, in particular the sodium salt of N,N-dimethylglycine, the thus dried composition and the use thereof.

BACKGROUND OF THE INVENTION

It is known to use specific amino acids or salts thereof as additive in animal feed. One particularly known representative of such amino acids or salts thereof is N,N-dimethyl glycinate salt.

For use of N,N-dimethyl glycinate in animal feed and animal feed premixes, N,N-dimethyl glycinate needs to be available on the market in a solid, dust-free, free-flowable form that has a stable composition. The stability of the composition during manufacturing and storage is jeopardized because N,N-dimethyl glycinate salts are hygroscopic when completely dry. Furthermore, they exist also as a non-hygroscopic hydrate salt, which however is difficult to obtain in an industrial manufacturing process.

N,N-dimethyl glycine can be manufactured via three routes, each requiring the use of a strong base, e.g. NaOH and hence resulting in the corresponding N,N-dimethyl glycinate salt as the end product.

All processes yield N,N-dimethyl glycinate salt as an aqueous solution or dispersion. However, N,N-dimethyl glycinate salt needs to be applied in the animal feed as a dry product. Several additives are used in a typical animal feed, mostly in relatively low quantities vs. the overall feed mass. For convenience of logistics and operations, premixtures are generally made of various dry components, to be added ultimately in the animal feed blending machine. Spraying additives as a liquid on top of is more complex and generally is only done for the bigger quantity additives.

Premixtures of feed additives are prepared typically by mixing the individual dry components in an appropriate blending device (e.g. Lödige mixer, or Nautta mixer) and transferring the product to bags. To run this operation smoothly, the components need to be free flowing, dust free and compatible with other ingredients. Compatibility refers to chemical compatibility in the sense that it should not react, but also physically, such that for instance no particle segregation occurs during mixing or transport. Additionally, the components also need to be stable in composition: that means that the composition of the individual components should not change during storage or handling, because they need to be metered into the premix at well-defined quantities. At the feed mill, the premixture is then typically fed into the blending system via a hopper or a silo. For this operation to run smoothly and safely, the components need to be dust free and free flowing as well.

To obtain a dustfree and free-flowable product, the N,N-dimethyl glycinate salt needs to be obtained as particles of sufficient, but not too large size and of homogeneous shape.

N,N-dimethyl glycinate salt can be obtained in dry form e.g. by crystallization, contact drying, spray drying, or fluidized bed drying.

N,N-dimethyl glycinate salt in dry form (N,N-dimethyl glycinate salt concentration of 99 wt-% and more) for example were found to be highly hygroscopic. In particular, sodium N,N-dimethyl glycinate (herein also referred to as Na-DMG) can take up to over 20% of water without a significant change in the look and feel of the product. Na-DMG for instance is not a deliquescent compound and water uptake does not pose problems with handling of the solid per se (e.g. stickiness). Industrially, it is however important to produce a constant composition of the product for reasons of dosing.

OBJECTS OF THE INVENTION

It was therefore an object of the present invention to provide one or more processes to obtain a composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, in a free-flowable form having a determined water content.

SUMMARY OF THE INVENTION

The object is solved by providing a process for drying a composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt in particular sodium N,N-dimethyl glycinate wherein M signifies an alkali metal cation, $R^1$, $R^2$ and $R^3$ signify independently from each other H, $C_1$ to $C_{18}$ alkyl residue, $C_1$ to $C_{18}$ alkenyl residue or $C_1$ to $C_{18}$ hydroxyalkyl residue, or wherein $R^1$ and $R^2$ form jointly together with the N-atom a heterocyclic 5- or 6-membered ring, comprising feeding a composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, into a fluidized bed dryer and subjecting the composition to a heat treatment by contacting the composition in the fluidized bed dryer with a drying gas stream, wherein during said heat treatment a solution or dispersion of the composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, is sprayed onto at least a portion of the composition present in the fluidized bed dryer.

The object is further solved by a process for drying a composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, wherein M signifies an alkali metal cation, $R^1$, $R^2$ and $R^3$ signify independently from each other H, $C_1$ to $C_{18}$ alkyl residue, $C_1$ to $C_{18}$ alkenyl residue or $C_1$ to $C_{18}$ hydroxyalkyl residue, or wherein $R^1$ and $R^2$ form jointly together with the N-atom a heterocyclic 5- or 6-membered ring, comprising feeding the composition comprising an alkali metal salt of a compound of general formula (I) $R^1R^2N$—$CHR^3$—COOM or formula (II) $R^1R^2N$—

$CHR^3CHR^3$—COOM, in particular N,N-dimethyl glycinate salt, into a fluidized bed dryer and subjecting the composition to a heat treatment in the fluidized bed dryer by contacting the composition with a drying gas stream, wherein the temperature of the composition in the fluidized bed during the heat treatment does not exceed 50° C.

In one embodiment of the processes according to the invention, a solution or dispersion of the composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, is sprayed onto the composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, present in the fluidized bed dryer during the heat treatment.

In one embodiment of the processes according to the invention, the composition comprising an alkali metal salt of a compound of general formula (I) $R^1R^2N$—$CHR^3$—COOM or formula (II) $R^1R^2N$—$CHR^3CHR^3$—COOM, comprises sodium N,N-dimethyl glycinate salt.

In one embodiment of the processes according to the invention, the spray temperature of the solution or dispersion of the composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, is at least 60° C.

In one embodiment of the processes according to the invention, comprising spraying a dispersion of the composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, having a solid content of at least 10 wt % based on the weight of the dispersion.

In one embodiment of the processes according to the invention, the process is conducted in a continuous manner or batch-wise.

In one embodiment of the processes according to the invention, the fluidized bed dryer is of conical shape.

In one embodiment of the processes according to the invention, the fluidized bed dryer is equipped with at least one particle size selector.

In one embodiment of the processes according to the invention, dust and/or small particles are removed from the bed of the composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, by the incoming drying gas.

In one embodiment of the processes according to the invention, the composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, is subjected to evaporative cooling in the fluidized bed dryer.

The composition according to the invention comprises a) at least 70 wt % of an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, wherein M signifies an alkali metal cation, $R^1$, $R^2$ and $R^3$ signify independently from each other H, $C_1$ to $C_{18}$ alkyl residue, $C_1$ to $C_6$ alkyl residue, $C_1$ to $C_{18}$ alkenyl residue, $C_1$ to $C_6$ alkenyl residue, $C_1$ to $C_6$ hydroxyalkyl residue or $C_1$ to $C_{18}$ hydroxyalkyl residue, or wherein $R^1$ and $R^2$ form jointly together with the N-atom a heterocyclic 5- or 6-membered ring, wherein the wt % are based on the total weight of the composition; b) at least 10 wt % water; wherein the wt % are based on the total weight of the composition, and wherein c) optionally one or more further compounds selected from alkali metal hydroxide, chloride, sulfate, glycolate, acetate, oxalate, or N-methyl glycine are present in the composition.

In one embodiment, the composition according to the invention comprises a) at least 75 wt % to 79 wt % of an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, wherein M signifies an alkali metal cation, $R^1$, $R^2$ and $R^3$ signify independently from each other H, $C_1$ to $C_{18}$ alkyl residue, $C_1$ to $C_{18}$ alkenyl residue or $C_1$ to $C_1$ hydroxyalkyl residue, or wherein $R^1$ and $R^2$ form jointly together with the N-atom a heterocyclic 5- or 6-membered ring, wherein the wt % are based on the total weight of the composition; b) 20 wt % to 24 wt % water, wherein the wt % are based on the total weight of the composition; c) optionally alkali metal hydroxide in an amount of at most 0.1 wt %; wherein the wt % are based on the total weight of alkali metal salt of the compound of general formulae (I) or (II) and, if present, the alkali metal hydroxide; d) optionally chloride in an amount of at most 75 ppm, or of at most 20 ppm, based on the total weight of the composition; e) optionally sulfate in an amount of at most 750 ppm, or of at most 50 ppm, based on the total weight of the composition; f) optionally glycolate in an amount of at most 750 ppm, or in an amount of 100 ppm to 750 ppm, based on the total weight of the composition; g) optionally acetate in an amount of at most 50 ppm, based on the total weight of the composition; h) optionally oxalate in an amount of at most 750 ppm, or in an amount of 200 ppm to 750 ppm, based on the total weight of the composition.

In one embodiment of the composition according to the invention, the composition comprises a) at least 70 wt % of an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, wherein M signifies an alkali metal cation, $R^1$, $R^2$ and $R^3$ signify independently from each other H, $C_1$ to $C_{18}$ alkyl residue, $C_1$ to $C_6$ alkyl residue, $C_1$ to $C_{18}$ alkenyl residue, $C_1$ to $C_6$ alkenyl residue, $C_1$ to $C_6$ hydroxyalkyl residue or $C_1$ to $C_{18}$ hydroxyalkyl residue, or wherein $R^1$ and $R^2$ form jointly together with the N-atom a heterocyclic 5- or 6-membered ring, wherein the wt % are based on the total weight of the composition; b) 20 wt % to 27 wt % water, wherein the wt % are based on the total weight of the composition; c) optionally alkali metal hydroxide in an amount of at most 0.1 wt %, wherein the wt % are based on the total weight of alkali metal salt of the compound of general formulae (I) or (II) and, if present, the alkali metal hydroxide; d) optionally chloride in an amount of at most 50 ppm, based on the total weight of the composition; e) optionally sulfate in an amount of at most 750 ppm, based on the total weight of the composition; f) optionally N-methylglycine in an amount of at least 0.025 wt %, wherein the wt % are based on the total weight of the composition.

In one embodiment, the composition according to the invention comprises a) 75 to 79 wt % of an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, wherein M signifies an alkali metal cation, $R^1$, $R^2$ and $R^3$ signify independently from each other H, $C_1$ to $C_{18}$ alkyl residue, $C_1$ to $C_6$ alkyl residue, $C_1$ to $C_{18}$ alkenyl residue, $C_1$ to $C_6$ alkenyl residue, $C_1$ to $C_6$ hydroxyalkyl residue or $C_1$ to $C_{18}$ hydroxyalkyl residue, or wherein $R^1$ and $R^2$ form jointly together with the N-atom a heterocyclic 5- or 6-membered ring, wherein the wt % are based on the total weight of the composition; b) 20 wt % to 27 wt % water, wherein the wt % are based on the total weight of the composition; c) optionally alkali metal hydroxide in an amount of at most 0.1 wt %, or not more than 0.08 wt %, or not more than 0.05 wt %, or not more than 0.015 wt %, wherein the wt % are based on the total weight of alkali metal salt of the compound of general formulae (I) or (II) and, if present, the alkali metal hydroxide; d) optionally N-methylglycine in an amount of 0.05 wt % to 0.7 wt %, wherein the wt % are based on the total weight of the composition.

In one embodiment, the composition according to the invention is obtained by one or both processes according to the invention.

Further, the present invention encompasses particles comprising or consisting of the composition according to the invention.

In one embodiment, the have a particle size distribution D50 of at least 400 μm and at most 600 μm.

The present invention further encompasses the use of the composition according to the invention or the particles according to the invention as additive in animal feed or animal feed premixes.

DETAILED DESCRIPTION OF THE INVENTION

Claimed herein are two alternative processes A and B for drying a composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, in particular sodium N,N-dimethyl glycinate salt:

Process A is a process for drying a composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, preferably sodium N,N-dimethyl glycinate salt, wherein M signifies an alkali metal cation, $R^1$, $R^2$ and $R^3$ signify independently from each other H, $C_1$ to $C_{18}$ alkyl residue, $C_1$ to $C_{18}$ alkenyl residue or $C_1$ to $C_{18}$ hydroxyalkyl residue, or wherein $R^1$ and $R^2$ form jointly together with the N-atom a heterocyclic 5- or 6-membered ring, comprising feeding a composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, preferably sodium N,N-dimethyl glycinate salt, into a fluidized bed dryer and subjecting the composition to a heat treatment by contacting the composition in the fluidized bed dryer with a drying gas stream, wherein during said heat treatment a solution or dispersion of the composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, preferably sodium N,N-dimethyl glycinate salt, is sprayed onto at least a portion of the composition present in the fluidized bed dryer.

Process B is a process for drying a composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, wherein M signifies an alkali metal cation, $R^1$, $R^2$ and $R^3$ signify independently from each other H, $C_1$ to $C_{18}$ alkyl residue, $C_1$ to $C_{18}$ alkenyl residue or $C_1$ to $C_{18}$ hydroxyalkyl residue, or wherein $R^1$ and $R^2$ form jointly together with the N-atom a heterocyclic 5- or 6-membered ring, comprising feeding the composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, into a fluidized bed dryer and subjecting the composition to a heat treatment in the fluidized bed dryer by contacting the composition with a drying gas stream, wherein the temperature of the composition in the fluidized bed during the heat treatment does not exceed 50° C.

Both processes A and B according to the invention have the advantage to obtain a dustfree, free flowable, stable composition particles comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt particles, having a homogeneous shape and advantageous particle size distribution by conducting only one industrially feasible drying step. Both processes A and B according to the invention have further the advantage to obtain composition particles comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt particles, having a defined water content.

In particular, it is possible to produce composition particles comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt particles, by the processes A and B according to the invention, wherein the composition particles comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt particles, have a water content of at most 30 weight %, or at most 25 weight %, or at most 20 wt %, or at most 17 wt %, or at most 15 wt %, or at most 12 wt %, or at most 10 wt %, or at most 7 wt %, or at most 5 wt %, or at most 2 wt %, or at most 1 wt %., each based on the total weight of the particles.

In one embodiment of process A according to the invention composition particles comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt particles, are produced, wherein the water content of the composition particles, in particular the N,N-dimethyl glycinate salt particles, is less than 10 weight %, preferably less than 2 weight %, more preferably 1 weight % or even less, each based on the total weight of the particles.

In one embodiment of process B according to the invention composition particles comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt particles, are produced, wherein the water content of the composition particles, in particular N,N-dimethyl glycinate salt particles, is less than 10 weight %, preferably less than 2 weight %, more preferably 1 weight % or even less, based on the total weight of the particles.

In one embodiment of process A according to the invention composition particles comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt particles, are produced, wherein the composition particles, in particular the N,N-dimethyl glycinate salt particles, preferably the sodium N,N-dimethyl glycinate salt particles, have a water content of at least 20 weight % and at most 23 weight %, preferably about 22 weight %, based on the total weight of the particles.

In one embodiment of process B according to the invention composition particles comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt particles, are produced, wherein the composition particles, in particular the N,N-dimethyl glycinate salt particles, preferably the sodium N,N-dimethyl glycinate salt particles, have a water content of at least 20 weight % and at most 23 weight %, preferably about 22 weight %, based on the total weight of the particles.

The composition comprising an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, obtained by the processes A and B according to the invention has therefore the advantage that the composition, in particular the N,N-dimethyl glycinate salt, can be used in animal feed premixes.

The term "N,N-dimethyl glycine" or "DMG" within the context of the present application means a compound of the following formula

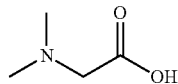

The term "composition particles comprising an alkali metal salt of a compound of general formula (I) $R^1R^2N$—$CHR^3$—COOM or formula (II) $R^1R^2N$—$CHR^3CHR^3$—COOM" as used within the context of the present application can be interchangeably used with the terms "composition according to the invention", "composition" or "product stream".

The composition according to the invention comprises at least an alkali metal salt of a compound of general formula (I) $R^1R^2N$—$CHR^3$—COOM or formula (II) $R^1R^2N$—$CHR^3CHR^3$—COOM. In an alternative embodiment, the composition according to the invention consists of an alkali metal salt of a compound of general formula (I) $R^1R^2N$—$CHR^3$—COOM or formula (II) $R^1R^2N$—$CHR^3CHR^3$—COOM.

The alkali metal salt of a compound of the general formula (I) $R^1R^2N$—$CHR^3$—COOM or formula (II) $R^1R^2N$—$CHR^3CHR^3$—COOM can be present in the composition according to the invention in an amount of at least 70 wt. %, or at least 73 wt. %, or at least 75 wt. %, or at least 76 wt. %, or at least 77 wt. %, or at least 80 wt. %, or at least 83 wt %, or at least 85 wt. %, or at least 90 wt %, or at least 93 wt %, or at least 95 wt %, or at least 99 wt %, wherein the wt % are based on the total weight of the composition.

In one embodiment of the composition according to the invention, the alkali metal salt of a compound of general formula (I) $R^1R^2N$—$CHR^3$—COOM or formula (II) $R^1R^2N$—$CHR^3CHR^3$—COOM is N,N-dimethyl glycinate salt which is fully dried. The term "fully dried N,N-dimethyl glycinate salt" within the context of the present application refers to N,N-dimethyl glycinate salt having a water content of at most 4.9 weight %, preferably at most 4 weight %, more preferably of at most 3.5 weight %, more preferably of at most 3 weight %, more preferably of at most 2 weight %, and most preferred of at most 1 weight %. Consequently, fully dried N,N-dimethyl glycinate salt contains at least 95.1 weight %, preferably at least 96 weight %, preferably at least 96.5 weight %, preferably at least 97 weight %, preferably at least 98 weight %, and most preferred at least 99 weight % N,N-dimethyl glycinate salt. This means that remaining water molecules contained in the fully dried N,N-dimethyl glycinate salt and the N,N-dimethyl glycinate salt, e.g. Na-DMG form together 100 weight % of fully dried N,N-dimethyl salt. The term "fully dried N,N-dimethyl glycinate salt" within the context of the present application therefore also refers to the product obtained by the processes A and B according to the invention.

Further, the alkali metal salt of a compound of the general formula (I) or formula (II) can be present in the composition according to the invention in an amount of at least 70 wt. %, or at least 73 wt. %, or at least 75 wt. %, or at least 76 wt. %, or at least 77 wt. %, and at most 90 wt. %, or at most 85 wt. %, or at most to 80 wt. %, or at most o 79 wt. %, or at most 78 wt. %, wherein the wt % are based on the total weight of the composition. Non-limiting examples of suitable ranges include from 70 wt. % to 90 wt. %, or from 70 wt. % to 85 wt. %, or from 70 wt. % to 80 wt. %, or from 70 wt. % to 79 wt. %, or from 70 wt. % to 78 wt. %, or from 70 wt. % to 77 wt. %, or from 70 wt. % to 76 wt. %, or from 70 wt. % to 75 wt. %, or from 73 wt. % to 90 wt. %, or from 73 wt. % to 85 wt. %, or from 73 wt. % to 80 wt. %, or from 73 wt. % to 79 wt. %, or from 73 wt. % to 78 wt. %, or from 73 wt. % to 77 wt. %, or from 73 wt. % to 76 wt. %, or from 73 wt. % to 75 wt. %, or from 75 wt. % to 90 wt. %, or from 75 wt. % to 85 wt. %, or from 75 wt. % to 80 wt. %, or from 75 wt. % to 79 wt. %, or from 75 wt. % to 78 wt. %, or from 75 wt. % to 77 wt. %, or from 76 wt. % to 90 wt. %, or from 76 wt. % to 85 wt. %, or from 76 wt. % to 80 wt. %, or from 76 wt. % to 79 wt. %, or from 76 wt. % to 78 wt. %, or from 76 wt. % to 77 wt. %, or from 77 wt % to 90 wt. %, or from 77 wt % to 85 wt. %, or from 77 wt. % to 80 wt. %, or from 77 wt % to 79 wt. %, wherein the wt % are based on the total weight of the composition. Quantities within a range of 73 wt. % to 80 wt. %, or from 73 wt. % to 79 wt. %, or from 73 wt. % to 78 wt. %, or from 73 wt. % to 77 wt. %, or from 75 wt. % to 80 wt. %, or from 75 wt. % to 79 wt. %, or from 75 wt. % to 78 wt. %, or from 75 wt. % to 77 wt. %, or from 76 wt. % to 80 wt. %, or from 76 wt. % to 79 wt. %, or from 76 wt. % to 78 wt. %, or from 76 wt. % to 77 wt. %, or from 77 wt. % to 80 wt. %, or from 77 wt. % to 79 wt. % are desirable, particularly from 75 wt. % to 79 wt. %, or from 75 wt. % to 78 wt. %, or from 75 wt. % to 77 wt. %, or from 76 wt. % to 79 wt. %, or from 77 wt. % to 79 wt. %, wherein the wt % are based on the total weight of the composition.

In general formula (I) $R^1R^2N$—$CHR^3$—COOM and formula (II) $R^1R^2N$—$CHR^3CHR^3$—COOM, M signifies an alkali metal cation, $R^1$, $R^2$ and $R^3$ signify independently from each other H, $C_1$ to $C_{18}$ alkyl residue, $C_1$ to $C_6$ alkyl residue, $C_1$ to $C_{18}$ alkenyl residue, $C_1$ to $C_6$ alkenyl residue, $C_1$ to $C_1$ hydroxy alkyl residue or $C_1$ to $C_6$ hydroxyalkyl residue, or wherein $R^1$ and $R^2$ form jointly together with the N-atom a heterocyclic 5- or 6-membered ring. In particular, M signifies $Li^+$, $Na^+$, $K^+$, or a mixture thereof, wherein $Na^+$ is particularly preferred.

One particularly preferred alkali metal salt of a compound of general formula (I) $R^1R^2N$—$CHR^3$—COOM is N,N-dimethyl glycinate salt, if $R^1=R^2$ signify $C_1$-alkyl residue and $R^3$ signifies H.

The term "N,N-dimethyl glycinate salt" as used within the context of the present application means the deprotonated form of DMG wherein the anionic charge of the N,N-dimethyl glycinate, located at the $CO_2$-moiety, is balanced by a cation stemming from the base used during the synthesis. Exemplarily for the N,N-dimethyl glycinate salt is shown below the embodiment wherein a sodium cation balances the anionic charge, i.e. the sodium N,N-dimethyl glycinate (also referred to herein as Na-DMG) is shown:

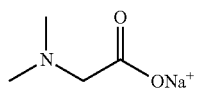

Suitable cations to balance the anionic charge of the N,N-dimethyl glycinate are alkali metal cations like Na$^+$ or K$^+$, wherein Na$^+$ is preferred.

The composition according to the invention can, besides the alkali metal salt of a compound of general formula (I) R$^1$R$^2$N—CHR$^3$—COOM or formula (II) R$^1$R$^2$N—CHR$^3$CHR$^3$—COOM, further comprise water. In one embodiment, the composition according to the invention consists of the alkali metal salt of a compound of general formula (I) R$^1$R$^2$N—CHR$^3$—COOM or formula (II) R$^1$R$^2$N—CHR$^3$CHR3-COOM and water.

The water content of the composition according to the invention can be at least 10 wt. %, or at least 15 wt. %, or at least 20 wt. %, or at least 21 wt. %, and in each case up to 30 weight %, or up to 27 wt. %, or up to 25 weight %, or up to 24 wt. %, or up to 23 wt. %, based on the total weight of the composition. Non-limiting examples of suitable ranges include from 10 wt. % to 30 wt. %, or from 10 wt. % to 27 wt. %, or from 10 wt. % to 25 wt. %, or from 10 wt. % to 24 wt. %, or from 10 wt. % to 23 wt. %, from 15 wt. % to 30 wt. %, or from 15 wt. % to 27 wt. %, or from 15 wt. % to 25 wt. %, or from 15 wt. % to 24 wt. %, or from 15 wt. % to 23 wt. %, or from 20 wt. % to 30 wt. %, or from 20 wt. % to 27 wt. %, or from 20 wt. % to 25 wt. %, or from 20 wt. % to 24 wt. %, or from 20 wt. % to 23 wt. %, from 21 wt. % to 30 wt. %, or from 21 wt. % to 27 wt. %, or from 21 wt. % to 25 wt. %, or from 21 wt. % to 24 wt. %, or from 21 wt. % to 23 wt. %, based on the total weight of the composition. Quantities of water within the range of from 15 wt. % to 27 wt. %, or from 15 wt. % to 25 wt. %, or from 20 wt. % to 27 wt. %, or from 20 wt. % to 25 wt. %, or from 20 wt. % to 24 wt. %, or from 21 wt. % to 27 wt. %, or from 21 wt. % to 25 wt. %, or from 21 wt. % to 24 wt. %, or from 21 wt. % to 23 wt. % are preferred, particularly quantities within a range of from 20 wt. % to 24 wt. %, or from 21 wt. % to 21 wt. % to 24 wt. %, or from 20 to 23 wt %, or from 21 wt. % to 23 wt. %, or 22 wt %, wherein the wt % are based on the total weight of the composition. In this context it is also herein referred to "composition hydrate particles".

In one embodiment of the composition according to the invention, the alkali metal salt of a compound of general formula (I) R$^1$R$^2$N—CHR$^3$—COOM or formula (II) R$^1$R$^2$N—CHR$^3$CHR$^3$—COOM is N,N-dimethyl glycinate salt which is hydrated. The term "N,N-dimethyl glycinate hydrate salt" within the context of the present application therefore refers to N,N-dimethyl glycinate salt having a water content of at least 5 weight % to at most 25 weight %, preferably of at least 10 weight % to at most 25 weight %, further preferably of at least 15 weight % to at most 25 weight %, most preferred of at least 20 weight % to at most 23 weight %, preferably about 22 weight %. Consequently, N,N-dimethyl glycinate hydrate salt contains at least 75 weight % and at most 95 weight %, preferably at least 75 weight % and at most 90 weight %, further preferably at least 75 weight % and at most 85 weight %, most preferred at least 77 weight % and at most 80 weight %, preferably about 78 weight % N,N-dimethyl glycinate. This means that the water molecules contained in the N,N-dimethyl glycinate hydrate salt and the N,N-dimethyl glycinate, e.g. Na-DMG form together 100 weight % of N,N-dimethyl hydrate salt based on the total weight of N,N-dimethyl glycinate and water. The term "N,N-dimethyl glycinate hydrate salt" within the context of the present application therefore refers to the product obtained by the processes A and B according to the invention.

The water content of the composition according to the invention, in particular of the N,N-dimethyl glycinate salt can be determined by a Karl-Fischer titration or a Mettler heat balance.

The composition according to the invention can optionally further comprise one or more further compounds selected from alkali metal hydroxide, chloride, sulfate, glycolate, acetate, oxalate, or N-methyl glycine.

The amount of alkali metal hydroxide optionally present in the composition according to the invention is less than 0.5 wt. %, and desirably not more than 0.1 wt %, or not more than 0.08 wt. %, or not more than 0.05% by weight, or not more than 0.025 wt. %, or not more than 0.015 wt. %, or not more than 0.01 wt. %, or not more than 0.0075 wt. %, or 0.00 wt % based on the total weight of the alkali metal salt of the compound of general formula (I) or (II) and alkali metal hydroxide. In addition, the amount of alkali metal hydroxide optionally present in the composition according to the invention can be at least greater than 0.00 wt. %, or at least 0.005 wt. %, or at least 0.01 wt. %, based on the total weight of the alkali metal salt of the compound of general formula (I) or (II) and alkali metal hydroxide. The presence of alkali metal hydroxide in the composition according to the invention can be detected by titration with 0.1 N HCl in MeCOH.

The amount of chloride compound(s) optionally present in the composition according to the invention is preferably not more than 75 ppm, or not more than 50 ppm, or not more than 30 ppm, or not more than 20 ppm, or not more than 10 ppm, or not more than 5 ppm, and can be 0 ppm, respectively beyond any detectable limit of chloride compound(s) (e.g. 0 ppm or below a detectable limit set to 0.5 ppm which is deemed equivalent to 0 ppm) based on the total weight of the composition.

The amount of sulfate compound(s) optionally present in the composition according to the invention, is preferably not more than 750 ppm, or not more than 500 ppm, or not more than 300 ppm, or not more than 100 ppm, or not more than 50 ppm, or not more than 10 ppm, and can be 0 ppm, respectively beyond any detectable limit of sulfate compound(s) (e.g. 0 ppm or below a detectable limit set to 0.5 ppm which is deemed equivalent to 0 ppm) based on the total weight of the composition.

The amount of glycolate compound(s) optionally present in the composition according to the invention is preferably at least 50 ppm, or at least 100 ppm, or at least 300 ppm, and up to 750 ppm, or up to 500 ppm, based on the total weight of the composition. Suitable ranges include 50 ppm to 750 ppm, or from 50 ppm to 500 ppm, or 100 ppm to 750 ppm, 100 ppm to 500 ppm, or from 300 ppm to 750 ppm, or from 300 ppm to 500 ppm.

The amount of acetate compound(s) optionally present in the composition according to the invention is preferably not more than 100 ppm, or not more than 50 ppm, or not more than 20 ppm, or not more than 10 ppm, based on the total weight of the composition.

The amount of oxalate compound(s), including alkali metal or dialkyl oxalates, optionally present in the composition according to the invention is preferably at least 100 ppm, or at least 200 ppm, or at least 300 ppm, and up to 750 ppm, or up to 500 ppm, based on the total weight of the composition. Suitable ranges include 100 ppm to 500 ppm, or 100 ppm to 750 ppm, 100 ppm to 500 ppm, or from 300 ppm to 750 ppm, or from 300 ppm to 500 ppm.

The amount of N-methylglycine, or sarcosine, optionally present in the composition according to the invention is preferably at least 0.025 wt. %, or at least 0.05 wt. %, or at least 0.1 wt. %, or at least 0.15 wt. %, and up to about 0.7 wt. %, or up to 0.5 wt. %, or up to 0.3 wt. %, based on the total weight of the composition. The presence of sarcosine can be due to some dealkylation of dimethylglycine on the catalysts used in the production process of DMG. Examples of quantities of N-methylglycine include from 0.025 wt. % to 0.7 wt. %, or from 0.025 wt. % to 0.5 wt. %, or 0.025 wt. % to 0.3 wt. %, 0.05 wt. % to 0.7 wt. %, or from 0.05 wt. % to 0.5 wt. %, or 0.05 wt. % to 0.3 wt. %, or from 0.1 wt. % to 0.7 wt. %, or from 0.1 wt. % to 0.5 wt. %, or 0.1 wt. % to 0.3 wt. %, 0.15 wt. % to 0.7 wt. %, or from 0.15 wt. % to 0.5 wt. %, or 0.15 wt. % to 0.3 wt. %, and based on the total weight of the composition.

The term "based on the total weight of the composition" as used within the context of the present application is to be understood such that the sum of weights of all components present in composition according to the invention is used as basis. E.g. if the composition according to the invention only consists of water and an alkali metal salt of general formula (I) or formula (II), then the total weight (=100 wt %) of the composition is the sum of the weights of water and the alkali metal salt of general formula (I) or formula (II) (e.g. 78 wt % water+22 wt % alkali metal salt of general formula (I) or formula (II)=100 wt % composition according to the invention).

In one embodiment of the composition according to the invention, the composition comprises a) at least 70 wt % of an alkali metal salt of a compound of general formula (I) $R^1R^2N$—$CHR^3$—COOM or formula (II) $R^1R^2N$—$CHR^3CHR^3$—COOM, in particular N,N-dimethyl glycinate salt, wherein M signifies an alkali metal cation, $R^1$, $R^2$ and $R^3$ signify independently from each other H, $C_1$ to $C_{18}$ alkyl residue, $C_1$ to $C_6$ alkyl residue, $C_1$ to $C_{18}$ alkenyl residue, $C_1$ to $C_6$ alkenyl residue, $C_1$ to $C_6$ hydroxyalkyl residue or $C_1$ to $C_{18}$ hydroxyalkyl residue, or wherein $R^1$ and $R^2$ form jointly together with the N-atom a heterocyclic 5- or 6-membered ring, wherein the wt % are based on the total weight of the composition; b) at least 10 wt % water wherein the wt % are based on the total weight of the composition; c) alkali metal hydroxide in a quantity of less than 0.5, or not more than 0.1% by weight, based on the weight of the alkali metal salt of the compound of the general formula (I) or formula (II) and, if any is present, the alkali metal hydroxide; d) a chloride content of not more than 75 ppm, based on the total weight of the composition; and e) a sulfate content of not more than 750 ppm, based on the total weight of the composition.

In one embodiment of the composition according to the invention, the composition comprises a) an alkali metal salt of a compound of the general formula (I) or formula (II) as described above present in an amount from 73 wt. % to 80 wt. %, or from 73 wt. % to 79 wt. %, or from 75 wt. % to 80 wt. %, or from 75 wt. % to 79 wt. %, or from 75 wt. % to 78 wt. %, or from 75 wt. % to 77 wt. %, preferably from 75 wt. % to 79 wt. %, or from 75 wt. % to 78 wt. %, or from 75 wt. % to 77 wt. %, based on the total weight of the composition; and b) water present in an amount from 20 wt. % to 27 wt. %, or from 20 wt. % to 25 wt. %, or from 20 wt. % to 24 wt. %, or from 21 wt. % to 24 wt. %, or from 21 wt. % to 23 wt. %, based on the total weight of the composition; c) an alkali metal hydroxide in a quantity of not more than 0.1% by weight, or not more than 0.08 wt. %, or not more than 0.05%, or not more than 0.015 wt. %, based on the total weight of the alkali metal salt of the compound of the general formula (I) or formula (II) and, if any is present, the alkali metal hydroxide; d) a chloride content, if any, of not more than 50 ppm, or not more 20 ppm, or not more than 10 ppm, based on the total weight of the composition; e) a sulfate content, if any, of not more than 750 ppm, or not more than 500 ppm, or not more than 50 ppm, or not more than 10 ppm, based on the total weight of the composition; f) optionally, glycolates in an amount from 100 ppm to 750 ppm, or from 300 ppm to 500 ppm, based on the total weight of the composition; g) optionally, acetates, if any, in an amount at not more than 50 ppm, or not more than 20 ppm, based on the total weight of the composition; and h) optionally, oxalates in an amount of 200 ppm to 750 ppm, or from 300 ppm to 500 ppm, based on the total weight of the composition.

In one embodiment of the composition according to the invention, the composition comprises a) an alkali metal salt of a compound of the general formula (I) or formula (II) as described above present in an amount of at least 70 wt. %, or from 73 wt. % to 80 wt. %, or from 73 wt. % to 79 wt. %, or from 75 wt. % to 80 wt. %, or from 75 wt. % to 79 wt. %, or from 75 wt. % to 78 wt. %, or from 75 wt. % to 77 wt. %, desirably from 75 wt. % to 79 wt. %, or from 75 wt. % to 78 wt. %, or from 75 wt. % to 77 wt. %, based on the total weight of the composition; and b) water present in an amount from 20 wt. % to 27 wt. %, or from 20 wt. % to 25 wt. %, or from 20 wt. % to 24 wt. %, or from 21 wt. % to 24 wt. %, or from 21 wt. % to 23 wt. %, based on the total weight of the composition; c) an alkali metal hydroxide in a quantity of not more than 0.1% by weight, or not more than 0.08 wt. %, or not more than 0.05%, or not more than 0.015 wt. %, based on the weight of the alkali metal salt of the compound of the general formula (I) or formula (II) and, if any is present, the alkali metal hydroxide; d) N-methylglycine, present in an amount of at least 0.025 wt, or at least 0.05 wt. %, or at least 0.1 wt. %, and in each case up to 0.7 wt. %, or up to 0.5 wt. %, or up to 0.3 wt. %, particularly from 0.05 wt. % to 0.5 wt. %, or 0.1 wt. % to 0.3 wt. %., based on the total weight of the composition; e) optionally a chloride content, if any, of not more than 50 ppm, or not more 20 ppm, or not more than 10 ppm, based on the total weight of the composition; and f) optionally a sulfate content, if any, of not more than 750 ppm, or not more than 500 ppm, or not more than 50 ppm, or not more than 10 ppm, based on the weight of the composition.

The terms "educt composition according to the invention" and "educt N,N-dimethyl glycinate salt" within the context of the present application means the composition according to the invention, in particular N,N-dimethyl glycinate salt, in the processes A and B according to the invention in the state prior to heat treatment (e.g. prior to applying a drying gas stream). The composition can be in solid form, e.g. in form of particles or powder, or in liquid form, e.g. in form of a solution or dispersion or suspension. In case, the composition according to the invention, in particular N,N-dimethyl glycinate salt, is used in solid form as educt, the water content of this composition is higher than the desired water content of the composition after the drying process. For example if it is desired to obtain a the composition according to the invention, in particular N,N-dimethyl glycinate salt, having a water content of at most 1 weight %, an educt composition with a water content of e.g. 25 weight % or even higher can be introduced to the heat treatment step in the fluidized bed dryer.

The composition according to the invention, in particular N,N-dimethyl glycinate salt, which is the product of the processes A and B according to the invention is obtained in solid form, preferably in form of particles.

It was found that the composition according to the invention, in particular N,N-dimethyl glycinate salt, obtained according to the processes A and B, in particular according to process B according to the invention and having a water content of at least 21 weight % and at most 23 weight %, preferably about 22 weight % is stable and non-hygroscopic at ambient conditions, i.e. the composition according to the invention, in particular N,N-dimethyl glycinate salt does not absorb water from the ambient atmosphere anymore on the one hand, and also does not release water to the ambience on the other hand. Therefore such composition according to the invention, in particular N,N-dimethyl glycinate salt, is particularly suitable to be used in animal feed premixes.

If the composition according to the invention, in particular N,N-dimethyl glycinate salt, having a water content of at least 21 weight % and at most 23 weight %, preferably about 22 weight % is used in subsequent applications, e.g. in animal premixes, this has the further advantage that energy which would have been consumed for obtaining a fully dried composition according to the invention, in particular N,N-dimethyl glycinate salt, can be saved.

When drying the composition according to the invention, in particular N,N-dimethyl glycinate salt, by conventional drying processes, no clear point in time when the composition according to the invention, in particular N,N-dimethyl glycinate salt, having a water content of at least 21 weight % and at most 23 weight % could be harvested, can be determined.

On the other hand, when trying to re-wet 99 weight % concentrated, solid composition according to the invention, in particular N,N-dimethyl glycinate salt, by exposing it to a stream of humid gas, it was found that water take-up occurs until the level of the composition according to the invention, in particular N,N-dimethyl glycinate salt, having a water content of at least 21 weight % and at most 23 weight %, preferably about 22 weight %. However, such a re-wet process to obtain the composition according to the invention, in particular N,N-dimethyl glycinate salt, having a water content of at least 21 weight % and at most 23 weight %, preferably about 22 weight % was found to be industrially impractical: time for re-absorption of water was long and the process was difficult to control to obtain a homogeneous product. Additionally, removing water first to re-introduce it in a second step is energy inefficient.

The processes A and B according to the invention, and in particular process B according to the invention, have therefore the advantage to obtain a homogeneous composition according to the invention, in particular N,N-dimethyl glycinate salt, i.e. that at least 80%, preferably at least 85%, further preferred at least 90%, further preferred at least 95%, and even more preferred at least 99% of the composition according to the invention, in particular the N,N-dimethyl glycinate salt, obtained by the processes A and B according to the invention have a water content of at least 21 wt % and at most 23 wt %, preferably about 22 wt %.

Further, the processes A and B according to the invention, and in particular process A according to the invention, have therefore the advantage to obtain a homogeneous composition according to the invention, in particular N,N-dimethyl glycinate salt, i.e. that at least 80%, preferably at least 85%, further preferred at least 90%, further preferred at least 95%, and even more preferred at least 99% of the composition according to the invention, in particular N,N-dimethyl glycinate salt, obtained by the processes A and B according to the invention have a water content of at most 20 wt %, preferably at most 17 wt %, preferably at most 15 wt %, preferably at most 12 wt %, more preferably at most 10 wt %, more preferably at most 7 wt %, more preferably at most 5 wt %, more preferably at most 2 wt %, and most preferred of at most 1 wt %.

In case a N,N-dimethyl glycinate salt is obtained by the processes A and B according to the invention, in particular obtained according to process B according to the invention and having a water content of at least 21 weight % and at most 23 weight %, preferably 22 weight % can also be regarded as N,N-dimethyl glycinate hydrate salt wherein in the crystal lattice two molecules water per molecule N,N-dimethyl glycinate salt can be observed.

In order to obtain the composition according to the invention, in particular N,N-dimethyl glycinate hydrate salt, respectively fully dried N,N-dimethyl glycinate salt, educt composition, in particular educt N,N-dimethyl glycinate salt, having a higher water content than the desired water content of the composition according to the invention, in particular the N,N-dimethyl hydrate salt, respectively the fully dried N,N-dimethyl glycinate salt after the drying process is fed into the fluidized bed dryer in liquid form or in solid form, preferably in form of an aqueous solution.

After the educt composition, in particular educt N,N-dimethyl glycinate salt, is fed into the fluidized bed dryer according to the processes A and B according to the invention, the educt composition, in particular educt N,N-dimethyl glycinate salt is subjected to a heat treatment within the fluidized bed dryer by contacting the educt composition, in particular the educt N,N-dimethyl glycinate salt, with a drying gas stream.

The drying gas stream which is fed into the fluidized bed dryer at the bottom of the fluidized bed dryer passes through the bed consisting of the educt composition, in particular the educt N,N-dimethyl glycinate salt particles, and thereby takes up water from the composition, in particular the N,N-dimethyl glycinate salt particles. Consequently, the temperature of the drying gas stream decreases while passing through the bed of the composition, in particular the N,N-dimethyl glycinate particles, and the relative humidity of the drying gas stream increases while passing through the bed of the composition, in particular the N,N-dimethyl glycinate particles, due to the water take-up from the composition, in particular the N,N-dimethyl glycinate particles.

In case an aqueous solution or dispersion of the composition, in particular the N,N-dimethyl glycinate salt, is used as educt, the aqueous solution or dispersion is fed into the fluidized bed dryer by means of spraying the solution or dispersion on top of the bed of the fluidized particles. At that time, the sprayed droplets of the aqueous solution or dispersion of the composition, in particular the N,N-dimethyl glycinate salt, impact solid composition, in particular solid N,N-dimethyl glycinate salt particles, in the fluidized bed, these particles are wetted. The wetted particles will then further dry because of the drying gas stream and as a result the composition particles, in particular the N,N-dimethyl glycinate salt particles, will grow in size. Alternatively, the sprayed droplets of the aqueous solution or dispersion of the composition, in particular the N,N-dimethyl glycinate salt, can be contacted with the incoming drying gas stream inside the fluidized bed dryer, and solidify due to water evaporation by the drying gas stream. Thus, new tiny composition particles, in particular N,N-dimethyl glycinate salt particles, are formed. The thus formed tiny composition particles, in particular N,N-dimethyl glycinate salt particles, can then further grow due to the impact of droplets of the aqueous solution or dispersion of the composition, in particular N,N-dimethyl glycinate salt, as described before.

Due to the water evaporation from the composition particles, in particular N,N-dimethyl glycinate salt particles, the particles are actually cooled. Consequently, the temperature of the composition particles, in particular N,N-dimethyl glycinate salt particles, which are dried in the fluidized bed dryer is lower than the temperature of the drying gas stream when entering the bed of the composition particles, in particular the bed of N,N-dimethyl glycinate salt particles. The temperature of the solid composition particles, in particular the solid N,N-dimethyl glycinate salt particles, in the fluidized bed dryer only reach the inlet temperature of the drying gas stream when composition particles, in particular N,N-dimethyl glycinate salt particles, are completely dried, respectively when evaporation of water has ceased. The temperature of the bed of solid composition particles, in particular solid N,N-dimethyl glycinate salt particles, hence will be dependent on the residual water content and will increase during the course of a drying cycle, in particular if operated in batch mode.

In process B according to the invention, temperature of the bed of composition particles, in particular the bed of N,N-dimethyl glycinate salt particles, is controlled to stay below 50° C., or below 48° C., or below 45° C., or below 43° C., or below 41° C. Non-limiting examples of suitable minimum temperatures include at least 35° C., or at least 37° C., or at least 39° C., or at least 40° C. It is most preferred to keep the temperature of the bed of composition particles, in particular the bed of N,N-dimethyl glycinate salt particles, between at most 50° C. and at least 35° C., or between at most 48° C. and at least 380, or between at most 45° C. and at least 40° C.

A minimum temperature of at least 35° C. is desirable for practical purposes because if the fluidized bed of composition particles, in particular the fluidized bed of N,N-dimethyl glycinate salt particles, has a temperature of below 35° C. the particles start to stick on the walls of the conventional materials used for a fluidized bed dryer. Further it was found that at temperatures above 50° C. fully dried composition particles (i.e. having a water content of at most 4.9 weight %, preferably at most 4 weight %, more preferably of at most 3.5 weight %, more preferably of at most 3 weight %, more preferably of at most 2 weight %, and most preferred of at most 1 weight %9, in particular fully dried N,N-dimethyl glycinate salt, are the predominating particles, whereas at temperatures of the fluidized bed of composition particles, in particular of N,N-dimethyl glycinate salt particles, of 50° C. and below, composition hydrate particles (e.g. having a water content of at least 21 wt % to at most 23 wt %, preferably 22 wt % based on the total weight of the composition), in particular N,N-dimethyl glycinate hydrate salt particles, are the predominating particles.

Temperature of the fluidized bed of composition particles, in particular of the fluidized bed of N,N-dimethyl glycinate salt particles, can be determined by commonly known means. It is possible to e.g. place a temperature sensor into the fluidized bed of the particles. It is further possible to e.g. measure the temperature of the particles directly after the particles have left the fluidized bed dryer.

This has the advantage that composition hydrate particles, in particular, N,N-dimethyl glycinate hydrate salt, can be homogeneously obtained, i.e. that after the drying process is finished, at least 80%, preferably at least 85%, further preferred at least 90%, further preferred at least 95%, and even more preferred at least 99% of the composition, in particular N,N-dimethyl glycinate salt, obtained by the processes A and B, in particular by process B according to the invention have a water content of at least 20 weight % and at most 23 weight %, preferably about 22 wt %.

The temperature of the composition particles, in particular N,N-dimethyl glycinate salt particles, in the fluidized bed can be influenced by various parameters, like the amount of water which is to be evaporated from the educt composition particles, in particular educt N,N-dimethyl glycinate salt. The amount of water to be evaporated depends on the feed rate as well as on the water content of the educt composition particles, in particular educt N,N-dimethyl glycinate salt which is fed into the fluidized bed dryer.

The temperature of the composition particles, in particular N,N-dimethyl glycinate salt particles, in the fluidized bed can further be influenced by the amount of the drying gas stream supplied into the fluidized bed dryer, or by the drying capacity of the drying gas stream. The capacity of the drying gas stream in turn depends on the inlet temperature of the drying gas stream, the moisture content of the inlet drying gas stream as well as on the outlet gas temperature.

Under the term "drying gas stream" within the context of the present application a gas stream is to be understood which is capable of drying solids, like the composition particles, or N,N-dimethyl glycinate salt particles. In particular, the drying gas stream is capable of taking water up from the solids, like the composition particles, or N,N-dimethyl glycinate salt particles, once the drying gas stream is in contact with said solids.

For example, the inlet temperature of the drying gas stream is preferably chosen to be as high as possible because then the drying gas stream has the highest capacity to take up water from the particles.

The moisture content of the inlet drying gas steam is preferably chosen to be as low as possible in order to maximize the water take-up abilities of the drying gas stream. Consequently, the moisture content of the drying gas stream prior to passing through the fluidized bed of the particles is lower than moisture content of the drying gas stream when having passed through the fluidized bed particles.

The velocity of the drying gas stream which is fed into the fluidized bed dryer is preferably high enough to fluidize the particles present in the fluidized bed dryer. Consequently, the velocity of the drying gas stream which is fed into the fluidized bed dryer can vary depending on the shape of the fluidized bed dryer and amount and size of particles loaded into the fluidized bed dryer.

Preferably, the velocity of the drying gas stream which is fed into the fluidized bed dryer is also high enough to remove dust and/or small particles from the particle bed.

As drying gas stream preferably normal, ambient air is used. It is however also possible to process the ambient air, e.g. to adapt the water content of the air, prior to feeding the air as drying gas stream into the fluidized bed dryer. Further, it is also possible to use inert gases as drying gas stream such as nitrogen. Or it is also possible to use a mixture of inert gas and ambient air as drying gas stream.

For the processes A and B according to the invention any commonly used fluidized bed dryer can be used. However, it is advantageous to use a fluidized bed dryer of conical shape, wherein the narrower part is closest to the bottom sieve plate. As such, the velocity of the drying gas stream decreases from the of bottom the fluidized bed dryer to the top of the fluidized bed dryer through the fluidized bed of particles which need to be dried.

This has the advantage that excessive blow off of fine particles is avoided. Furthermore, the higher velocity of the drying gas stream close to the bottom sieve plate allows fluidization of the bigger particles and prevents loading of solid material onto the bottom sieve plate. A further advantage is that the higher velocity of the drying gas at the bottom of the fluidized bed dryer allows a controlled transport of dust and/or small particles out of the bed of particles. Since the velocity of the drying gas stream decreases when passing through the bed of particles, the removed dust and/or small particles can settle in the upper part of the fluidized bed dryer. It is also possible that the removed dust and/or small particles which are blown out by the outgoing drying gas stream from the bed of particles be recovered from the outgoing drying gas stream by suitable means such as cyclones, filters or wet scrubbers. Cyclones or filters are preferred as they allow recovering the removed dust and/or small particles in solid form. This has the advantage that such recovered dust and/or small particles may be recycled into the fluidized bed dryer, in which they will have the opportunity to grow further when they are impacted by liquid droplets of a solution or dispersion of the composition, in particular of N,N-dimethyl glycinate salt.

The processes A or B according to the invention can be performed batchwise or in a continuous manner.

The term "batchwise manner", respectively "batchwise" within the context of the present application is commonly known by a skilled person and means that educt composition, in particular educt N,N-dimethyl glycinate salt is preferably used in solid form, and the amount of the composition particles, in particular N,N-dimethyl glycinate salt particles, which are to be dried are fed into the fluidized bed dryer all at once. The particles are floated by a stream of drying gas which typically passes through a bottom sieve plate prior to being contacted with the particles. By passing through the bed of floated particles the drying gas stream takes up and thus removes excess water contained in the particles.

During the processes A or B according to the invention performed in a batchwise manner all particles like for example N,N-dimethyl glycinate hydrate salt particles, respectively fully dried N,N-dimethyl glycinate salt particles, remain in the fluidized bed dryer until the drying processes A or B according to the invention are completed, i.e. until at least 80%, preferably at least 90%, preferably at least 95%, more preferably at least 99% of the particles have reached the desired water content.

After the drying processes A or B according to the invention are finished, the particles are removed from the fluidized bed dryer and the next charge particles which are to be dried is fed into the fluidized bed dryer.

The term "continuous manner" within the context of the present application is also commonly known by the skilled person and means that the processes A and B according to the invention are conducted continuously. Educt composition, in particular N,N-dimethyl glycinate salt, either in solid form or in liquid form, preferably in form of an aqueous solution or dispersion, is continuously fed into the fluidized bed dryer, and subjected there to the drying processes A or B according to the invention. While the particles are floating through the fluidized bed dryer, they are contacted with the drying gas stream and thereby excess water is removed from the particles until particles having the desired water content are obtained. The particles are then continuously removed from the fluidized bed dryer.

The advantage of the processes A or B according to the invention being performed in a continuous manner is that during the process, all process parameters (e.g. temperature of the fluidized bed of the composition, in particular N,N-dimethyl glycinate salt) remain essentially constant if the input parameters (e.g. temperature and quantity of the inlet drying gas stream) remain unchanged. A further advantage is that a high throughput is achieved, since intermediate stops as in the batchwise performed operation mode are avoided. In a continuously operated drying process, it is however essential that the product does not stick to the walls or other internals of the fluidized bed dryer to avoid loading over during longer periods of operation.

In a continuously operated fluidized bed dryer according to processes A and B according to the invention, the particles have an average residence time during which they are contacted with the drying gas stream of preferably 10 minutes to 5 hours, more preferably of 1 to 3 hours.

For an efficient continuous operation, the particles need to be withdrawn continuously from the fluidized bed dryer. This can be done by any suitable means.

Preferably only such particles, are extracted that have the desired particle size range. This can be done by so-called particle size selectors that are able to extract composition (hydrate) particles, in particular N,N-dimethyl glycinate hydrate salt particles, respectively fully dried N,N-dimethyl glycinate salt particles, above a certain particle size from the fluidized bed. This can for instance be achieved by creating a hole into the bottom sieve plate that allows particles which hit the bottom to go out. A suitable stream of the drying gas is applied through the hole from outside to the inside of the fluidized bed dryer, such that only the heavier (bigger) particles can make the downward movement through the hole.

It is advantageous to spray an aqueous solution or dispersion of the composition, in particular of N,N-dimethyl glycinate salt, onto the particles present in the fluidized bed dryer during the processes A or B according to the invention. The droplets of the solution or dispersion of the composition, in particular of N,N-dimethyl glycinate salt, impact the floating particles, and essentially make them grow as drying continues and more composition, in particular N,N-dimethyl glycinate salt solidifies. Some droplets can dry by themselves, without impacting other particles (similar to what happens in a spray drying tower) and hence constitute new (fine) particles that afterwards can grow further due to the droplet impact process.

Spraying of a solution or dispersion of an aqueous solution or dispersion of the composition, in particular of N,N-dimethyl glyciante salt, onto the bed particles present in the fluidized bed dryer has the advantage that an essentially homogeneous water content particles leaving the fluidized bed dryer can be achieved. Further, spraying of a solution or dispersion of an aqueous solution or dispersion of the composition, in particular of N,N-dimethyl glycinate salt, onto the bed of particles present in the fluidized bed dryer has the advantage that the desired particle size of the particles leaving the fluidized bed dryer can be achieved, i.e. that the particles leaving the fluidized bed dryer have an essentially homogeneous particle size distribution. Even further, spraying of a solution or dispersion of an aqueous solution or dispersion of the composition, in particular of N,N-dimethyl glycinate salt onto the bed of particles present in the fluidized bed dryer has the advantage that an essentially homogeneous shape of the particles leaving the fluidized bed dryer can be achieved, i.e. that particles leaving the fluidized bed dryer have an essentially spherical shape. This improves in consequence the flowability characteristics of the composition particles, in particular N,N-dimethyl glycinate salt particles, which makes it easier to handle the particles.

The spraying can be performed by commonly known means, e.g. by using spraying nozzles. The spraying nozzles can be positioned inside the fluidized bed of floating particles or can be positioned above the fluidized bed of floating particles.

The spraying can be done if the processes A or B according to the invention are performed in batchwise or in a continuous manner.

In case of the batchwise performance of the processes A or B according to the invention, the spraying can be continued until a predefined amount of solid particles is present in the fluidized bed dryer (for instance, defined by the dimensions and specifications of the fluidized bed dryer). Then a period of post drying can be applied, in which only the drying gas stream is supplied to the fluidized bed dryer and no solution or dispersion of the composition, in particular of N,N-dimethyl glycinate salt. Finally, the heat-treated particles are removed from the fluidized bed dryer, and the processes A or B according to the invention can be restarted.

Since a solution or dispersion of the composition, in particular N,N-dimethyl glycinate salt, is introduced into the fluidized bed dryer during the processes A or B according to the invention, this process mode can also be referred to as "fed batch" or "semi continuous".

In one embodiment of processes A and B according to the invention water instead of an aqueous solution or dispersion of the composition, in particular of N,N-dimethyl glycinate salt, is sprayed onto the bed of the particles present in the fluidized bed dryer. This has the advantage to maintain or increase the water content of the particles present in the fluidized bed dryer.

In order to interrupt the drying processes A or B according to the invention at the right point in time, namely when the desired water content particles are achieved, it is advantageous to control the temperature of the particles inside the fluidized bed. E.g. if the particles reach essentially the same temperature as the drying gas stream, essentially all water is evaporated from the particles.

If the processes A or B according to the invention are performed in a continuous manner, a continuous supply of educt composition, in particular educt N,N-dimethyl glycinate salt takes place. This has the advantage that further water is introduced into the fluidized bed dryer and thus available at any given moment in order to allow particles that have been over dried, i.e. that have a water content of less than the desired water content, to take up water again such that the water content increases again.

If educt composition, in particular educt N,N-dimethyl glycinate salt is used as an aqueous solution or dispersion, respectively the solution or dispersion of the composition, in particular of N,N-dimethyl glycinate salt, which is sprayed onto the fluidized bed of particles, the solution or dispersion is preferably added as an aqueous solution or dispersion as it is obtained from the chemical synthesis of the composition, in particular the N,N-dimethyl glycinate salt. Prior to adding the solution or dispersion to the fluidized bed dryer, it can be purified to remove unconverted starting materials or side products arising during the synthesis.

The solution or dispersion of the composition, in particular of N,N-dimethyl glycinate salt, can be added as an aqueous solution, or as a dispersion with solids content of at least 10 wt %, preferably at least 15 wt %, preferably at least 17 wt %, preferably at least 19 wt %, preferably at least 20 wt %, preferably at least 22 wt %, preferably at least 25 wt %, preferably at least 28 wt %, preferably at least 30 wt %, preferably at least 32 wt %, preferably at least 35 wt %, preferably at least 38 wt %, preferably at least 40 wt % or even higher, each based on the weight if the solution or dispersion and solids. A high solids content of the solution or dispersion of the composition, in particular of N,N-dimethyl glycinate salt, is advantageous, because less water needs to be evaporated in the fluidized bed dryer, resulting in lower energy consumption and higher capacity of the fluidized bed dryer. However, at higher concentration, crystallization and solid formation may occur if the liquid is handled above the solubility limits. Solubility of the composition, in particular of N,N-dimethyl glycinate salt, in water is dependent on the temperature. The solubility in water increases with increasing temperature of the solution or dispersion.

Preferably, the solution or dispersion of the composition, in particular of N,N-dimethyl glycinate salt, is preheated to avoid formation of crystallization and solid formation in the solution or dispersion feed lines and on the spraying means, like spray nozzles. The spray temperature of the composition, in particular of the N,N-dimethyl glycinate salt, (the temperature of the salt solution or dispersion fed to the spray nozzles or other spray means) can be at least 60° C., or at least 65° C., or at least 70° C., or at least 75° C., or at least 80° C.

Preferably, the solution or dispersion of the composition, in particular of N,N-dimethyl glycinate salt, is sprayed into the fluidized bed of particles. Spraying can be effectuated by spray nozzles as already mentioned, in which the solution or dispersion of the composition, in particular of N,N-dimethyl glycinate salt, is pushed through a narrow orifice, causing droplets to be formed.

Suitable spray means are for instance single fluid spray nozzles, in which pressurized solution or dispersion of the composition, in particular of N,N-dimethyl glycinate salt is pushed through the orifice, or two-fluid nozzles in which the solution or dispersion of the composition, in particular of N,N-dimethyl glycinate salt and a gas (e.g. compressed gas) are pushed through the nozzle. Multiple spray nozzles can be used to achieve the necessary flow rates and spraying homogeneity throughout the fluidized bed. Spraying can occur downwards on top of the fluidized bed of solid particles or upwards from within the fluidized bed of solid particles. Spraying upwards from within the fluidized bed of solid particles is preferred.

Due to the spraying, the particles are constantly growing because of the impact with liquid droplets of the composition, in particular N,N-dimethyl glycinate salt, solution or dispersion. Preferably only those particles are extracted that have the desired particle size range. Extraction can be done by using e.g. particle size selectors that are able to extract particles above a certain size from the fluidized bed. This can for instance be achieved by creating a hole into the bottom sieve plate that allows particles that hit the bottom to go out. A suitable stream of the drying gas is applied through the hole, such that only the heavier (bigger) particles can make the downward movement through the hole.

In one embodiment, composition, in particular N,N-dimethyl glycinate salts, are subjected to evaporative cooling in the fluidized bed dryer.

Heat-treated particles that are extracted from the fluidized bed dryer can further be classified according to their size, for instance by sieving.

It is an advantage of the processes A or B according to the invention to obtain particles having a well-defined particle size distribution. Consequently, the flowability characteristics of the particles which have been dried by the processes A or B according to the invention could be improved. Improved flowability characteristics facilitate the use of heat-treated particles in animal premixes.

In particular, the heat-treated composition particles, in particular the heat-treated N,N-dimethyl glycinate salt particles, have preferably a particle size of at least 100 µm, or at least 200 µm, or at least 250 µm, or at least 300 µm, or at least 350 µm, or at least 400 µm, and at most 450 µm, or at most 500 µm, or at most 550 µm, or at most 600 µm, or at most 700 µm, or at most 800 µm.

Heat-treated particles that are found to be too small, i.e. having a particles size of below 100 µm (causing dust or unfavourable compactation during storage) can be reinjected into the fluidized bed where they can grow further to bigger particle size. Heat-treated particles that are too big, i.e. having a particle size of more than 800 µm, aggregates of particles or lumps can be milled by any suitable milling device and be reinjected as well into the dryer or onto the classifying sieves.

Sieving of heat-treated particles having the desired particle size can be done by using e.g. two sieves having the desired particles sizes as holes. The heat-treated particles are poured onto the first sieve having the bigger holes. The particles which cannot pass through the sieve hole have a particle size exceeding the defined upper limit of the desired particle size range. If the heat-treated particles have passed through the first sieve, but fallen through the subsequently following second sieve having holes corresponding to the lower defined limit of the particle range, their particle size is too small. All heat-treated particles staying on top of the second sieve have a particle size within the desired particle size range.

Preferably composition particles, in particular N,N-dimethyl glycinate hydrate salt particles, respectively fully dried N,N-dimethyl glycinate salt particles, heat-treated according to the processes A or B according to the invention have a d50 value of between 400 µm and 600 µm. E.g. if the d50 value of one batch of heat-treated particles according to the invention is 450 µm, then half of the weight of the particles will be smaller than 450 µm and half of the weight of the particles will be bigger than 450 µm.

Generally, the particle size distribution of one batch of heat-treated particles can be determined by sieve analysis which is commonly known by a skilled person.

In particular, the composition hydrate particles, in particular N,N-dimethyl glycinate hydrate salt particles, obtained by the processes A or B according to the invention remain stable, i.e. the water content of at least 21 weight % and at most 23 weight %, preferably 22 wt %, remain the same for 24 h in a layer of 5 mm at a temperature of 20° C. and relative gas humidity of 85%.

The heat-treated particles can be used in animal feed and animal feed premixes.

EXAMPLES

The examples are to be understood as illustrating the process according to the invention. The examples are however not to be construed as limiting the scope of the invention.

Example 1

A 40 weight % aqueous solution or dispersion of sodium N,N-dimethyl glycinate salt (Na-DMG) was prepared and spray granulated on a AGT 400 fluidized bed spray granulation drying pilot line (Glatt; bottom screen area: 0.1 m$^2$; diameter processing chamber: 400 mm; diameter expansion chamber: 800 mm; height: 3600 mm). The fluidized bed dryer is further equipped with a cyclone to recover and recycle fine dust particles of N,N-dimethyl glycinate salt from the exhaust drying gas.

The educt solution or dispersion of Na-DMG was sprayed into the fluidized bed in the drying chamber with a gas/liquid pressure nozzle. The spray gas temperature was room temperature and the spray gas pressure was 2 to 3 bar. The temperature of the educt Na-DMG solution or dispersion was room temperature and the feed rate (peristaltic pump) was 500 to 600 g/min.

The drying process was run continuously, i.e. there was a constant supply of educt Na-DMG solution or dispersion and a constant withdrawal of dried Na-DMG particles from the fluidized bed dryer by means of a particle size selector. Na-DMG particle growth was effectuated by the constant supply of Na-DMG solution through the spray nozzle.

A drying gas stream was supplied to the fluidized bed dryer through the bottom sieve plate (0.1 m$^2$) at 1000 m$^3$/h. The temperature of the inlet drying gas stream was at most 140° C. The resulting temperature of the Na-DMG particles in the fluidized bed was measured using a temperature probe installed into the dense zone of the fluidized bed. The temperature of the fluidized bed of Na-DMG particles was kept constant (tolerance range: ±3 to 5° C.).

If a steady state was obtained dried Na-DMG particles leaving the fluidized bed dryer were collected and the residual water content was measured using a heat balance. The results are summarized in Table 1.

TABLE 1

| Sample No | Temperature (° C.) of Na-DMG particles in fluidized bed during heat treatment | Water content (% wt) of dried Na-DMG particles |
|---|---|---|
| 1 | 65-68 | 0.37 |
| 2 | 60-65 | 0.28 |
| 3 | 51-53 | 1.34 |
| 4 | 43-48 | 7.38 |
| 5 | 40-45 | 17.40 |
| 6 | 35-40 | 25.00 |

Example 2

The results of Example 1 were used to obtain continuous production of Na-DMG hydrate particles on an industrial size dryer with similar layout (bottom sieve plate 3.4 m$^2$). An aqueous Na-DMG solution or dispersion containing approximately 25 wt % of Na-DMG salt was spray into the dying chamber of the fluidized bed dryer by multiple gas/liquid nozzles. The fluidized bed dryer is further equipped with a cyclone to recover and recycle fine dust particles of N,N-dimethyl glycinate salt from the exhaust drying gas. The inlet drying gas had a temperature of approximately 190° C. at a flow of approximately 32 tonnes per hour. The outlet drying gas was approximately 55° C. throughout the trial assuring a temperature of the fluidized bed of 40-45° C.

Na-DMG hydrate salt particles of sufficient size were collected from the fluidized bed through the particle size selector in the bottom plate. The Na-DMG hydrate salt particles which were removed from the fluidized bed dryer through the particles size selector in the bottom sieve plate are subjected to a sieving operation. Na-DMG hydrate salt particles having a particle size <200 µm were collected and recycled into the drying chamber. Na-DMG hydrate salt particles having a particle >800 µm were milled and then also recycled into the drying chamber.

In total, 50 tons of Na-DMG hydrate salt particles were produced at an average production rate of 0.8 ton per hour. For every ton of Na-DMG hydrate salt particles collected, a sample was taken and analyzed for residual water content via KF titration. The average water content was 21.43 wt % with a standard deviation of 0.28 wt %. The d50 value of the Na-DMG hydrate salt particles obtained was determined by sieve analysis. The average value was 460 µm with a standard deviation of 20 µm.

This example shows that at large scale, the process can be carefully controlled to selectively obtain the Na-DMG hydrate salt particles at a consistent residual water content and average particle size.

Example 3

1000 L of an aqueous Na-DMG solution or dispersion (19 wt %) was preheated to 60° C. and fed into the AGT 400 fluidized bed dryer. The same set-up as described in Example 1 was used. The quantity of the inlet drying gas stream was 1100 m$^3$/h and the inlet drying gas stream temperature was 240° C. The drying process was run continuously. A stable operation was achieved with an outlet gas temperature of about 73° C. resulting in an average temperature of the fluidized bed of Na-DMG particles of 109° C.

Dried Na-DMG particles were continuously withdrawn from the fluidized bed dryer to obtain a stable bed. The drying process was running stable and without any operational problems.

About 10 wt % of oversize Na-DMG particles (particle size above 800 μm) was generated during the drying process. These particles were recovered from the fluidized bed of Na-DMG particles by means of continuous sieving, milled and reintroduced into the fluidized bed dryer.

During the continuous operation of the fluidized bed dryer dried Na-DMG particles leaving the fluidized bed dryer were collected and examined for their particles size distribution by means of stacked sieve analysis and their residual water content by means of a heat balance measurement. The results are summarized in Table 2:

TABLE 2

| Sample No | Sieve analysis (μm, wt %) | | | | | | | Water content (% wt) of dried Na-DMG particles |
|---|---|---|---|---|---|---|---|---|
| | <100 | 100-200 | 200-355 | 355-400 | 400-500 | 500-800 | >800 | |
| 1 | 0.0 | 1.3 | 5.2 | 3.0 | 12.2 | 69.9 | 8 | 1.3 |
| 2 | 0.2 | 2.2 | 11.6 | 5.4 | 22.6 | 58.2 | 0.4 | 1.8 |
| 3 | 0.3 | 2.3 | 7.5 | 3.6 | 15.9 | 70.1 | 0.2 | 1.4 |
| 4 | 1.4 | 4.6 | 12.2 | 4.4 | 13.0 | 59.4 | 4.8 | 2.0 |
| 5 | 0.0 | 1.6 | 5.3 | 2.5 | 3.8 | 72.5 | 14.2 | 1.7 |
| 6 | 0.0 | 3.4 | 11.6 | 4.7 | 13.8 | 63.1 | 3.4 | 1.7 |
| 7 | 0.0 | 5.9 | 22.2 | 10.8 | 21.1 | 38.6 | 1.4 | 1.4 |
| 8 | 0.0 | 3.2 | 11.2 | 8.2 | 28.2 | 48.8 | 0.4 | 1.5 |
| 9 | 0.4 | 4.2 | 11.6 | 6.2 | 17.4 | 59.8 | 0.8 | 1.4 |

It could be shown that it is possible using the drying processes A or B according to the invention to obtain dried Na-DMG particles having a well-defined particle size distribution.

Example 4

A sample of Na-DMG particles having a residual water content of 22 wt % was subjected to a Flow Function Test using a Brookfield Powder Flow Tester. In this test, the unconfined failure strength $\sigma_c$ is measured for different levels of consolidation stress $\sigma_1$. The flow function ff is defined as ff=$\sigma_1/\sigma_c$ and is a measure of the flowability of the sample. The sample is rated from not flowing to free flowing using following criteria:

| | |
|---|---|
| ff < 1 | non flowing |
| 1 < ff < 2 | very cohesive |
| 2 <= ff < 4 | cohesive |
| 4 <= ff < 10 | easy flowing |
| 10 <= ff | free flowing |

The analysed sample of Na-DMG particles have a particle size distribution as follows:

| | [μm] | | | | | |
|---|---|---|---|---|---|---|
| | <45 | 45-250 | 250-500 | 500-710 | 710-800 | 800-1000 | >1000 |
| Particles [wt %] | 0.0 | 0.2 | 7.8 | 36.2 | 39.2 | 15.8 | 0.2 |

The Na-DMG particles had a flow function of 171.5 and therefore, the particles were rated as "free flowing".

For comparison reasons, a part of the Na-DMG particles were milled and sieved using a 45 μm aperture sieve. The particles passing the sieve were collected and subjected to a second Flow Function Test, wherein a flow function of 1,8 was obtained and the particles were rated as "very cohesive".

Example 4 demonstrates the superior flowability properties of the Na-DMG particles manufactured using the process according to the invention.

The invention claimed is:

1. A process for drying a composition comprising a compound of general formula (I) $R^1, R^2N-CHR^3-COOM$ or general formula (II) $R^1R^2N-CHR^3CHR^3-COOM$,
    wherein M signifies an alkali metal cation, and $R^1$, $R^2$ and $R^3$ signify independently from each other H, $C_1$ to $C_{18}$ alkyl residue, $C_1$ to $C_{18}$ alkenyl residue or $C_1$ to $C_{18}$ hydroxyalkyl residue, or $R^1$ and $R^2$ form jointly together with the N-atom a heterocyclic 5- or 6-membered ring,
    (i) the process comprising feeding the composition into a fluidized bed dryer and subjecting the composition to a heat treatment by contacting the composition in the fluidized bed dryer with a drying gas stream,
    wherein during said heat treatment, a solution or dispersion of the composition is sprayed onto at least a portion of the composition present in the fluidized bed dryer;
    wherein the dispersion has a solids content of at least 10 wt % based on the weight of the dispersion; and
    (ii) extracting heat-treated particles comprising the compound from the fluidized bed dryer, wherein the heat-treated particles have a water content of at least 21 wt % and at most 23 wt %.

2. A process for drying a composition comprising a compound of general formula (I) $R^1, R^2N-CHR^3-COOM$ or general formula (II) $R^1R^2N-CHR^3CHR^3-COOM$,
    wherein M signifies an alkali metal cation, and $R^1$, $R^2$ and $R^3$ signify independently from each other H, $C_1$ to $C_{18}$ alkyl residue, $C_1$ to $C_{18}$ alkenyl residue or $C_1$ to $C_{18}$ hydroxyalkyl residue, or $R^1$ and $R^2$ form jointly together with the N-atom a heterocyclic 5- or 6-membered ring, the process comprising feeding the composition into a fluidized bed dryer and subjecting the composition to a heat treatment in the fluidized bed dryer by contacting the composition with a drying gas stream, wherein the temperature of the composition in the fluidized bed during the heat treatment does not exceed 50° C.

3. The process according to claim 2, wherein a solution or dispersion of the composition is sprayed onto the composition present in the fluidized bed dryer during the heat treatment.

4. The process according to claim 1, wherein the composition comprises sodium N,N-dimethyl glycinate.

5. The process according to claim 1, wherein the temperature of the solution or dispersion is at least 60° C.

6. The process according to claim 1, wherein the process is conducted in a continuous manner or batch-wise.

7. The process according to claim 1, wherein the fluidized bed dryer is of conical shape.

8. The process according claim 1, wherein the fluidized bed dryer is equipped with at least one particle size selector.

9. The process according to claim 1, wherein dust and/or small particles are removed from a fluidized bed of particles of the composition in the fluidized bed dryer by the incoming drying gas.

10. The process according to claim 1, wherein the composition is subjected to evaporative cooling in the fluidized bed dryer.

11. Particles comprising a composition comprising:
   a) at least 70 wt % of a compound of general formula (I) $R^1R^2N$—$CHR^3$—COOM or general formula (II) $R^1R^2N$—$CHR^3CHR^3$—COOM, wherein M signifies an alkali metal cation, and $R^1$, $R^2$ and $R^3$ signify independently from each other H, $C_1$ to $C_{18}$ alkyl residue, $C_1$ to $C_6$ alkyl residue, $C_1$ to $C_{18}$ alkenyl residue, $C_1$ to $C_6$ alkenyl residue, $C_1$ to $C_6$ hydroxyalkyl residue or $C_1$ to $C_{18}$ hydroxyalkyl residue, or $R^1$ and $R^2$ form jointly together with the N-atom a heterocyclic 5- or 6-membered ring, wherein the wt % is based on the total weight of the composition;
   b) at least 10 wt % of water;
   wherein the wt % is based on the total weight of the composition, and wherein
   c) if present, alkali metal hydroxide in a quantity of not more than 0.1% by weight, based on the weight of the compound of the general formula (I) or general formula (II) and the alkali metal hydroxide; and
   d) if any is present, a chloride content of not more than 75 ppm, based on weight of the composition; and
   e) if any is present, a sulfate content of not more than 750 ppm, based on weight of the composition,
   wherein the particles have a particle size distribution D50 of at least 400 μm and at most 600 μm.

12. The particles according to claim 11 wherein the composition comprises:
   a) 75 wt % to 79 wt % of the compound of the general formula (I) or general formula (II), wherein the wt % are based on the total weight of the composition;
   b) 20 wt % to 24 wt % water, wherein the wt % are based on the total weight of the composition;
   c) if present, alkali metal hydroxide in a quantity of not more than 0.1% by weight, based on the weight of the compound of the general formula (I) or general formula (II) and the alkali metal hydroxide;
   d) if any is present, a chloride content of not more than 20 ppm, based on weight of the composition;
   e) if any is present, a sulfate content of not more than 50 ppm, based on weight of the composition;
   f) optionally glycolate in an amount of at most 750 ppm, based on the total weight of the composition;
   g) optionally acetate in an amount of at most 50 ppm, based on the total weight of the composition;
   h) optionally oxalate in an amount of at most 750 ppm, based on the total weight of the composition.

13. The particles according to claim 11, wherein the composition comprises:
   a) at least 70 wt % of the compound of the general formula (I) or general formula (II), wherein the wt % is based on the total weight of the composition;
   b) 20 wt % to 27 wt % of water, wherein the wt % are based on the total weight of the composition;
   c) alkali metal hydroxide in an amount of at most 0.1 wt %, wherein the wt % is based on the total weight of the compound of general formulae (I) or (II) and, if present, the alkali metal hydroxide;
   d) N-methylglycine, present in an amount of at least 0.025 wt. %, based on the weight of the composition;
   e) optionally chloride in an amount of at most 50 ppm, based on the total weight of the composition; and
   f) optionally sulfate in an amount of at most 750 ppm, based on the total weight of the composition.

14. The particles according to claim 13, wherein the composition comprises:
   a) 75 to 79 wt % of the compound of general formula (I) or general formula (II), wherein the wt % are based on the total weight of the composition;
   b) 20 wt % to 25 wt % of water, wherein the wt % are based on the total weight of the composition;
   c) alkali metal hydroxide in an amount of at most 0.1 wt %, wherein the wt % is based on the total weight of the compound of general formulae (I) or (II) and, if present, the alkali metal hydroxide; and
   d) N-methylglycine in an amount of 0.05 wt % to 0.7 wt %, wherein the wt % are based on the total weight of the composition.

15. The process according to claim 2, wherein the composition comprises sodium N,N-dimethyl glycinate.

16. The process according to claim 1, which further comprises extracting heat-treated particles comprising the compound from the fluidized bed dryer,
   wherein the heat-treated particles have a particle size distribution D50 of at least 400 μm and at most 600 μm.

17. The process according to claim 2, which further comprises extracting heat-treated particles comprising the compound from the fluidized bed dryer,
   wherein the heat-treated particles have a particle size distribution D50 of at least 400 μm and at most 600 μm.

18. The process according to claim 2, which further comprises extracting heat-treated particles comprising the compound from the fluidized bed dryer,
   wherein the heat-treated particles have a water content of at least 21 wt % and at most 23 wt %.

* * * * *